(12) United States Patent
Maguire et al.

(10) Patent No.: US 8,282,675 B2
(45) Date of Patent: Oct. 9, 2012

(54) ANTI-BACKOUT MECHANISM

(75) Inventors: Paul S. Maguire, Hope Valley, RI (US); Douglas L. Hester, Raynham, MA (US)

(73) Assignee: DePuy Spine, Inc., Raynham, MA (US)

( * ) Notice: Subject to any disclaimer, the term of this patent is extended or adjusted under 35 U.S.C. 154(b) by 1124 days.

(21) Appl. No.: 12/019,926

(22) Filed: Jan. 25, 2008

(65) Prior Publication Data
US 2009/0192553 A1 Jul. 30, 2009

(51) Int. Cl.
- *A61B 17/80* (2006.01)
- *A61B 17/04* (2006.01)
- *A61B 17/86* (2006.01)
- *A61F 2/08* (2006.01)
- *F16B 37/04* (2006.01)
- *F16B 39/04* (2006.01)
- *F16B 19/00* (2006.01)
- *F16B 21/00* (2006.01)

(52) U.S. Cl. ........ 606/289; 606/310; 411/103; 411/316; 411/360; 411/508; 411/512

(58) Field of Classification Search ................ 606/289, 606/294, 310, 319; 411/103, 105, 112, 114, 411/194, 255, 316, 322, 342, 347, 352, 360, 411/409, 422, 508, 512, 514, 530, 549, 552, 411/979, 21, 22; 403/370, 372
See application file for complete search history.

(56) References Cited

U.S. PATENT DOCUMENTS

| | | | |
|---|---|---|---|
| 867,429 A | 10/1907 | Simmerman | |
| 1,091,674 A | 3/1914 | Lee | |
| 1,784,026 A * | 12/1930 | Olson | 411/81 |
| 1,845,428 A * | 2/1932 | Llewellyn | 411/81 |
| 2,077,804 A | 4/1937 | Morrison | |
| 2,685,877 A | 8/1954 | Dobelle | |
| 3,016,077 A * | 1/1962 | Yocum | 411/81 |
| 3,953,140 A * | 4/1976 | Carlstrom | 403/258 |

(Continued)

FOREIGN PATENT DOCUMENTS

EP 1348390 10/2003

(Continued)

OTHER PUBLICATIONS

Law, et al., "Caudo-Cephalad Loading of Pedicle Screws: Mechanisms of Loosening and Methods of Augmentation," SPINE 1993, vol. 18, No. 16, pp. 2438-2443.

(Continued)

*Primary Examiner* — Kevin T Truong
*Assistant Examiner* — David Bates
(74) *Attorney, Agent, or Firm* — Nutter McClennen & Fish LLP

(57) ABSTRACT

Methods and devices for locking a fastener in a thru-bore are provided herein. In one exemplary embodiment, a spinal anchor is provided that includes a bone engaging fastener, an anti-backout mechanism, and a locking mechanism. The anti-backout mechanism can be movable between a retracted position in which it is disposed within the fastener and a deployed position in which is extends from the bone engaging fastener. The locking mechanism can be matable to the bone engaging fastener and can be configured to move the anti-backout mechanism from the retracted position to the deployed position. In the deployed position, the anti-backout mechanism can prevent the bone engaging fastener from backing out of a thru-bore in a spinal plate.

20 Claims, 6 Drawing Sheets

U.S. PATENT DOCUMENTS

| | | | |
|---|---|---|---|
| 4,579,491 A | 4/1986 | Kull | |
| 4,636,121 A * | 1/1987 | Miller | 411/21 |
| 4,716,893 A | 1/1988 | Fischer et al. | |
| 4,760,843 A | 8/1988 | Fischer et al. | |
| 4,790,304 A | 12/1988 | Rosenberg | |
| 4,871,289 A | 10/1989 | Choiniere | |
| 4,943,292 A | 7/1990 | Foux et al. | |
| 5,053,036 A | 10/1991 | Perren et al. | |
| 5,057,111 A | 10/1991 | Park | |
| 5,127,914 A | 7/1992 | Calderale et al. | |
| 5,151,103 A | 9/1992 | Tepic et al. | |
| 5,176,682 A | 1/1993 | Chow | |
| 5,209,753 A | 5/1993 | Biedermann et al. | |
| 5,269,784 A | 12/1993 | Mast | |
| 5,364,399 A | 11/1994 | Lowery et al. | |
| 5,472,452 A * | 12/1995 | Trott | 606/232 |
| 5,474,553 A | 12/1995 | Baumgart et al. | |
| 5,478,342 A * | 12/1995 | Kohrs | 606/310 |
| 5,489,210 A * | 2/1996 | Hanosh | 433/173 |
| 5,501,684 A | 3/1996 | Schlapfer et al. | |
| 5,520,690 A | 5/1996 | Errico et al. | |
| 5,534,027 A | 7/1996 | Hodorek | |
| 5,578,034 A | 11/1996 | Estes | |
| 5,578,035 A | 11/1996 | Lin | |
| 5,601,558 A | 2/1997 | Torrie et al. | |
| 5,607,426 A | 3/1997 | Ralph et al. | |
| 5,607,428 A | 3/1997 | Lin | |
| 5,611,688 A | 3/1997 | Hanosh | |
| 5,643,265 A | 7/1997 | Errico et al. | |
| 5,643,321 A * | 7/1997 | McDevitt | 606/232 |
| 5,702,391 A | 12/1997 | Lin | |
| 5,735,853 A | 4/1998 | Olerud et al. | |
| 5,741,258 A | 4/1998 | Klaue et al. | |
| 5,759,184 A | 6/1998 | Santangelo | |
| 5,769,852 A | 6/1998 | Br.ang.nemark | |
| 5,797,912 A | 8/1998 | Runciman et al. | |
| 5,810,823 A | 9/1998 | Klaue et al. | |
| 5,843,082 A | 12/1998 | Yuan et al. | |
| 5,849,004 A * | 12/1998 | Bramlet | 606/232 |
| 5,876,402 A | 3/1999 | Errico et al. | |
| 5,902,303 A | 5/1999 | Eckhof et al. | |
| 5,904,683 A | 5/1999 | Pohndorf et al. | |
| 5,931,621 A * | 8/1999 | Griffith et al. | 411/255 |
| 5,931,838 A | 8/1999 | Vito | |
| 5,954,722 A | 9/1999 | Bono | |
| 5,976,139 A | 11/1999 | Bramlet | |
| 6,017,345 A | 1/2000 | Richelsoph | |
| 6,030,389 A | 2/2000 | Wagner et al. | |
| 6,036,693 A | 3/2000 | Yuan et al. | |
| 6,039,740 A | 3/2000 | Olerud et al. | |
| 6,077,264 A | 6/2000 | Chemello et al. | |
| 6,168,597 B1 | 1/2001 | Biedermann et al. | |
| 6,183,474 B1 | 2/2001 | Bramlet et al. | |
| 6,206,882 B1 | 3/2001 | Cohen | |
| 6,235,033 B1 | 5/2001 | Brace et al. | |
| 6,261,291 B1 | 7/2001 | Talaber et al. | |
| 6,273,889 B1 | 8/2001 | Richelsoph | |
| 6,322,562 B1 | 11/2001 | Wolter et al. | |
| 6,331,179 B1 | 12/2001 | Freid et al. | |
| 6,402,756 B1 | 6/2002 | Ralph et al. | |
| 6,423,067 B1 | 7/2002 | Eisermann | |
| 6,428,542 B1 | 8/2002 | Michelson | |
| 6,443,954 B1 | 9/2002 | Bramlet et al. | |
| 6,447,513 B1 | 9/2002 | Griggs | |
| 6,447,546 B1 * | 9/2002 | Bramlet et al. | 623/17.16 |
| 6,454,769 B2 | 9/2002 | Wagner et al. | |
| 6,575,975 B2 | 6/2003 | Brace et al. | |
| 6,595,993 B2 | 7/2003 | Donno et al. | |
| 6,599,290 B2 | 7/2003 | Bailey et al. | |
| 6,602,255 B1 | 8/2003 | Campbell et al. | |
| 6,648,889 B2 | 11/2003 | Bramlet et al. | |
| 6,660,008 B1 | 12/2003 | Foerster et al. | |
| 6,668,688 B2 | 12/2003 | Zhao et al. | |
| 6,679,883 B2 | 1/2004 | Hawkes et al. | |
| 6,695,846 B2 | 2/2004 | Richelsoph et al. | |
| 6,890,334 B2 | 5/2005 | Brace et al. | |
| 6,932,834 B2 | 8/2005 | Lizardi et al. | |
| 6,945,975 B2 | 9/2005 | Dalton | |
| 6,964,664 B2 | 11/2005 | Freid et al. | |
| 6,979,334 B2 | 12/2005 | Dalton | |
| 6,989,013 B2 | 1/2006 | Pisharodi | |
| 7,001,389 B1 | 2/2006 | Navarro et al. | |
| 7,052,499 B2 | 5/2006 | Steger et al. | |
| 7,118,572 B2 | 10/2006 | Bramlet et al. | |
| 7,381,213 B2 | 6/2008 | Lizardi | |
| 7,879,036 B2 * | 2/2011 | Biedermann et al. | 606/62 |
| 7,905,908 B2 * | 3/2011 | Cragg et al. | 606/279 |
| 2001/0021851 A1 | 9/2001 | Eberlein et al. | |
| 2002/0058939 A1 | 5/2002 | Wagner et al. | |
| 2003/0187440 A1 | 10/2003 | Richelsoph et al. | |
| 2003/0199876 A1 * | 10/2003 | Brace et al. | 606/69 |
| 2003/0208204 A1 | 11/2003 | Bailey et al. | |
| 2003/0225409 A1 | 12/2003 | Freid et al. | |
| 2004/0019353 A1 | 1/2004 | Freid et al. | |
| 2004/0087951 A1 | 5/2004 | Khalili | |
| 2004/0097935 A1 | 5/2004 | Richelsoph et al. | |
| 2004/0106925 A1 | 6/2004 | Culbert | |
| 2004/0127896 A1 | 7/2004 | Lombardo et al. | |
| 2004/0127897 A1 | 7/2004 | Freid et al. | |
| 2004/0127899 A1 | 7/2004 | Konieczynski et al. | |
| 2004/0127900 A1 | 7/2004 | Konieczynski et al. | |
| 2004/0127904 A1 | 7/2004 | Konieczynski et al. | |
| 2004/0172022 A1 | 9/2004 | Landry et al. | |
| 2004/0181227 A1 | 9/2004 | Khalili | |
| 2004/0193157 A1 | 9/2004 | Falahee | |
| 2004/0193162 A1 | 9/2004 | Bramlet et al. | |
| 2004/0254579 A1 | 12/2004 | Buhren et al. | |
| 2005/0004574 A1 | 1/2005 | Muckter | |
| 2005/0010218 A1 | 1/2005 | Dalton | |
| 2005/0010219 A1 | 1/2005 | Dalton | |
| 2005/0027296 A1 | 2/2005 | Thramann et al. | |
| 2005/0033298 A1 | 2/2005 | Hawkes et al. | |
| 2005/0049593 A1 | 3/2005 | Duong et al. | |
| 2005/0059971 A1 * | 3/2005 | Michelson | 606/69 |
| 2005/0143737 A1 | 6/2005 | Pafford et al. | |
| 2005/0149027 A1 | 7/2005 | Campbell et al. | |
| 2005/0154392 A1 | 7/2005 | Medoff et al. | |
| 2005/0192577 A1 | 9/2005 | Mosca et al. | |
| 2005/0228386 A1 | 10/2005 | Ziolo et al. | |
| 2005/0228387 A1 | 10/2005 | Paul | |
| 2005/0267474 A1 | 12/2005 | Dalton | |
| 2005/0273105 A1 | 12/2005 | Konieczynski et al. | |
| 2005/0277937 A1 | 12/2005 | Leung et al. | |
| 2005/0283152 A1 | 12/2005 | Lindemann et al. | |
| 2006/0009770 A1 | 1/2006 | Speirs et al. | |
| 2006/0015104 A1 | 1/2006 | Dalton | |
| 2006/0025768 A1 | 2/2006 | Iott et al. | |
| 2006/0100626 A1 | 5/2006 | Rathbun et al. | |
| 2006/0116678 A1 | 6/2006 | Impellizzeri | |
| 2006/0122602 A1 | 6/2006 | Konieczynski et al. | |
| 2006/0122604 A1 | 6/2006 | Gorhan et al. | |
| 2006/0149249 A1 | 7/2006 | Mathoulin et al. | |
| 2006/0149256 A1 | 7/2006 | Wagner et al. | |
| 2006/0149258 A1 | 7/2006 | Sousa | |
| 2006/0161157 A1 | 7/2006 | Mosca et al. | |
| 2007/0038210 A1 | 2/2007 | Yaldo | |
| 2007/0038219 A1 | 2/2007 | Matthis et al. | |
| 2007/0073295 A1 | 3/2007 | Biedermann et al. | |
| 2007/0198018 A1 | 8/2007 | Biedermann et al. | |
| 2008/0086130 A1 | 4/2008 | Lake et al. | |
| 2008/0086131 A1 | 4/2008 | Daly et al. | |
| 2008/0183220 A1 | 7/2008 | Glazer et al. | |
| 2008/0255618 A1 | 10/2008 | Fisher et al. | |
| 2009/0099601 A1 | 4/2009 | Aferzon et al. | |

FOREIGN PATENT DOCUMENTS

| | | |
|---|---|---|
| WO | WO-9416634 | 8/1994 |
| WO | 0067653 A1 | 11/2000 |

OTHER PUBLICATIONS

Grubb, et al., "Biomechanical Evaluation of Anterior Cervical Spine Stabilization," SPINE 1998, vol. 23, No. 8, pp. 886-892.

Spivak, et al., "The Effect of Locking Fixation Screws on the Stability of Anterior Cervical Plating", SPINE 1999, vol. 24, No. 4, pp. 334-338.

Foley, et al., "Percutaneous pedicle screw fixation of the lumbar spine", Neurosurg Focus 10 (4), Article 10, pp. 108, 2001.

Yang, et al., "Biomechanical comparision of the stable efficacy of two anterior plating systems", Clinical Biomechanics, vol. 18(6), pp. 59-66, Jul. 2003.

Keller, et al., "The ComPact UniLock 2.0/2.4 system and its clinical application in small animal orthopedics", Vet Comp Orthop Traumatol, pp. 83-93, Feb. 2005.

Lehmann, et al., "Biomechanical comparison of anterior cervical spine locked and unlocked plate-fixation systems", Eur Spine J. 2005, vol. 14, pp. 243-249.

Suk, et al., "Unilateral Versus Bilaterial Pedicle Screw Fixation in Lumbar Spinal Fusion", SPINE, vol. 25, No. 14, pp. 1843-1847, 2000.

Chen, et al., "Biomechanical Analysis of Unilateral Fixation With Interbody Cages", SPINE, vol. 30, No. 4, pp. E92-E96, 2005.

Harris, et al., "Transforaminal Lumbar Interbody Fusion", SPINE, vol. 29, No. 4, pp. E65-E70, 2004.

* cited by examiner

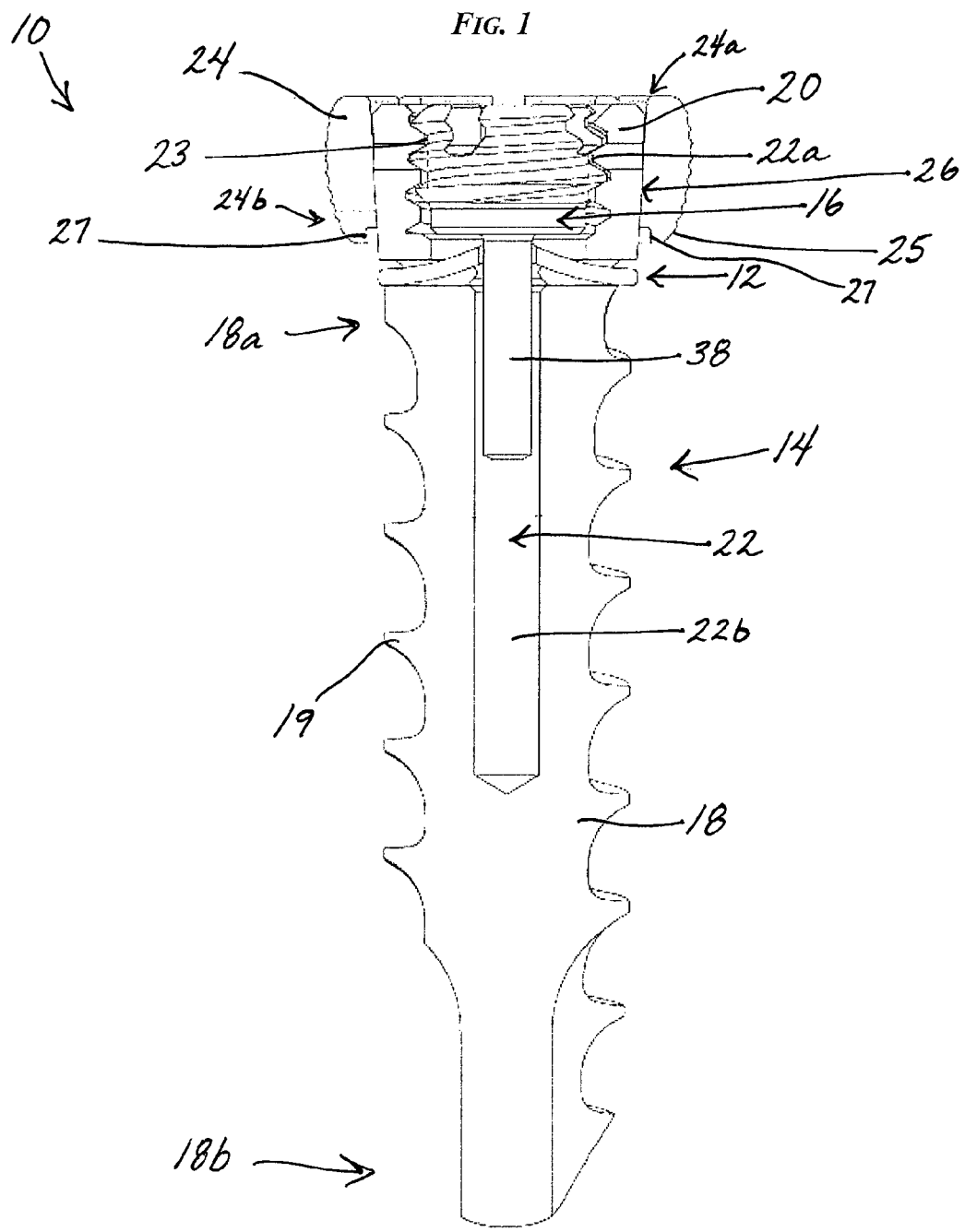

ANTI-BACKOUT MECHANISM

FIELD

The present disclosure relates to bone fixation methods and devices, and in particular to methods and devices for preventing a bone engaging fastener from backing out of a bone plate.

BACKGROUND

Bone fixation devices are useful for promoting the proper healing of injured or damaged vertebral bone segments caused by trauma, tumor growth, or degenerative disc disease. These external fixation devices immobilize the injured bone segments to ensure the proper growth of new osseous tissue between the damaged segments. External bone fixation devices such as these often include internal bracing and instrumentation to stabilize the spinal column to facilitate the efficient healing of the damaged area without deformity or instability, while minimizing any immobilization and post-operative care of the patient.

One type of external bone fixation device is an osteosynthesis plate, more commonly referred to as a bone plate, that can be used to immobilize adjacent skeletal parts such as vertebral bones. Typically, the fixation plate is a rigid metal or polymeric plate positioned to span bones or bone segments that require immobilization with respect to one another. The plate is fastened to the respective bones, using anchors such as bone screws, so that the plate remains in contact with the bones and fixes them in a desired position. Anterior cervical plates, for instance, can be useful in providing the mechanical support necessary to keep vertebral bodies in proper position and bridge a weakened or diseased area such as when a disc, vertebral body or spinal fragment has been removed. These anterior cervical plates usually include a rigid bone plate having a plurality of screw openings. The openings are either holes or slots that allow for freedom of screw movement. The bone plate is placed against the damaged vertebral bodies and bone screws are used to secure the bone plate to the spine, usually with the bone screws being driven into the vertebral bodies.

While current bone plates and bone screws are effective, unintentional loosening of the screws can reduce the effectiveness of an anterior construct and can result in erosion and irritation of the esophagus.

Accordingly, there is a need for methods and devices for preventing a bone screw from backing out of a bone plate.

SUMMARY

Methods and devices are provided for locking a bone engaging fastener in a spinal plate. In one embodiment, a spinal anchor is provided and includes a bone engaging fastener, an anti-backout mechanism, and a locking mechanism. The anti-backout mechanism can be disposed within the bone engaging fastener and biased to a retracted position in which the anti-backout mechanism is fully contained within the bone engaging fastener. In use, the anti-backout mechanism can be movable between the retracted position and a deployed position in which the anti-backout mechanism extends from the bone engaging fastener. The locking mechanism can be matable to the bone engaging fastener and configured to move the anti-backout mechanism from the retracted position to the deployed position.

The bone engaging fastener can have a variety of configurations but can generally be configured to sit in a thru-bore in a spinal plate and can include a shank with a head formed thereon. In one exemplary embodiment, the head of the bone engaging fastener can include a bore formed therein for receiving the locking mechanism. The bone engaging fastener can also include a cavity therein and having cut-outs extending through opposed sidewalls of the fastener. The cut-outs can extend substantially perpendicular to a central axis of the fastener and they can be configured to allow opposed ends of the anti-backout mechanism to extend radially outward from the fastener when the anti-backout mechanism is in the deployed position. In another embodiment, a bushing can be disposed around the head of the bone engaging fastener. The head can be configured to expand and engage the bushing when the locking mechanism is mated to the bone engaging fastener.

A variety of configurations are also available for the locking mechanism. For example, in one exemplary embodiment, the locking mechanism can be a set screw. The set screw can optionally include an alignment mechanism such as elongate member extending distally therefrom. In use, the locking mechanism can be configured to apply a distally directed force to the anti-backout mechanism when the locking mechanism is disposed within the bore to move the anti-backout mechanism to the deployed configuration.

The anti-backout mechanism can also have a variety of configurations, but in one exemplary embodiment, the anti-backout mechanism can be a spring, such as a leaf spring. In general, the spring can be in a natural state, such as a bent configuration, in the retracted position. The anti-backout mechanism can also be configured such that it extends substantially perpendicular to a central axis of the bone engaging fastener and is substantially planar in the deployed configuration.

In another exemplary embodiment, a spinal fixation kit is provided and can include a spinal plate having at least one thru-bore formed therein, a bone engaging fastener disposable within the at least one thru-bore in the spinal plate, and a locking mechanism that is matable to the bone engaging fastener and configured to cause an anti-backout mechanism disposed within the bone engaging fastener to extend from the fastener to thereby prevent the fastener from backing out of the thru-bore in the spinal plate. In one aspect, the thru-bore in the spinal plate can contain a bushing disposed therein for seating a portion of the bone engaging fastener.

Methods for locking a bone engaging fastener in a spinal plate are also provided. In one embodiment, the method can include inserting a bone engaging fastener through a thru-bore in a spinal plate and applying a locking mechanism to the bone engaging fastener to deploy an anti-backout mechanism in the bone engaging fastener to cause the anti-backout mechanism to extend outward from the bone engaging fastener thereby preventing the bone engaging fastener from backing out of the thru-bore such that the bone engaging fastener is locked within the thru-bore in the spinal plate. In an exemplary embodiment, the locking mechanism can be configured to apply a distally directed force to the anti-backout mechanism to cause the anti-backout mechanism to move from a retracted position in which the anti-backout mechanism is fully contained within the bone engaging fastener to a deployed position in which the anti-backout mechanism extends from the bone engaging fastener. Applying the locking mechanism can include threading the locking mechanism into a bore formed in a head of the bone engaging fastener. In one embodiment, applying the locking mechanism can cause the head of the bone engaging fastener to expand and engage a bushing disposed therearound and seated in the thru-bore in the spinal plate. Applying the locking mechanism can also cause the anti-backout mechanism to become substantially planar. Upon deployment, the anti-backout mechanism can engage a bone contacting surface of the spinal plate or a bone contacting surface of a bushing disposed in a thru-bore of the plate.

BRIEF DESCRIPTION OF THE DRAWINGS

Various exemplary embodiments disclosed herein will be more fully understood from the following detailed description taken in conjunction with the accompanying drawings, in which:

FIG. 1 is a cross-sectional view of one exemplary embodiment of spinal anchor having an anti-backout mechanism;

DETAILED DESCRIPTION

Figure 2A:
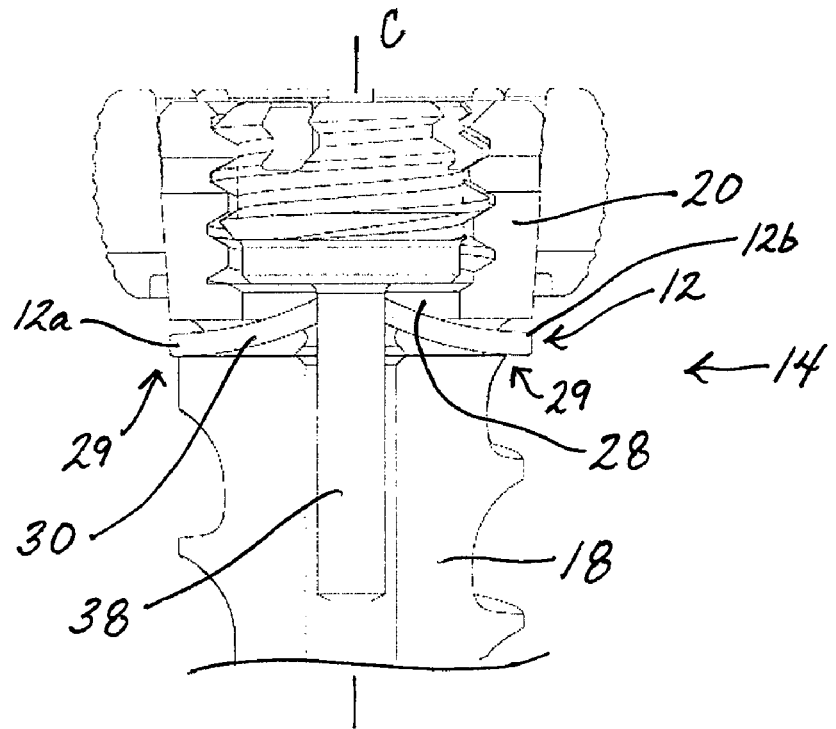
FIG. 2A is a cross-sectional view of a proximal portion of the spinal anchor shown in FIG. 1 showing the anti-backout mechanism fully within the spinal anchor in a retracted position.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope is defined solely by the claims. The features illustrated or described in connection with one exemplary embodiment may be combined with the features of other embodiments. Such modifications and variations are intended to be included within the scope of the present application.

Methods and devices for locking a bone engaging fastener in a bone plate are provided herein. In particular, the methods and devices provide an anti-backout mechanism to prevent a bone engaging fastener from backing out of a thru-bore in a bone plate. In an exemplary embodiment, as shown in FIG. 1, a spinal anchor 10 is provided that includes a bone engaging fastener 14, an anti-backout mechanism 12, and a locking mechanism 16. The bone engaging fastener 14 can have a head that is configured to sit in a thru-bore in a spinal plate. The anti-backout mechanism can be disposed within the bone engaging fastener, and it can be movable between a retracted position and a deployed position. In the retracted position, the anti-backout 12 mechanism can be fully contained within the bone engaging fastener 14, and in the deployed position the anti-backout mechanism 12 can extend from the bone engaging fastener 14. The locking mechanism 16 can be matable to the bone engaging fastener 14, and it can be configured to move the anti-backout mechanism 12 from the retracted position to the deployed position. In the deployed position, the anti-backout mechanism 12 can prevent the bone engaging fastener 14 from backing out of a thru-bore in a spinal plate. A person skilled in the art will appreciate that, while a spinal screw and plate are discussed herein, the anti-backout mechanism can be incorporated into any fastener for retaining the fastener within any thru-bore and application is not limited to medical products.

Figure 4A:
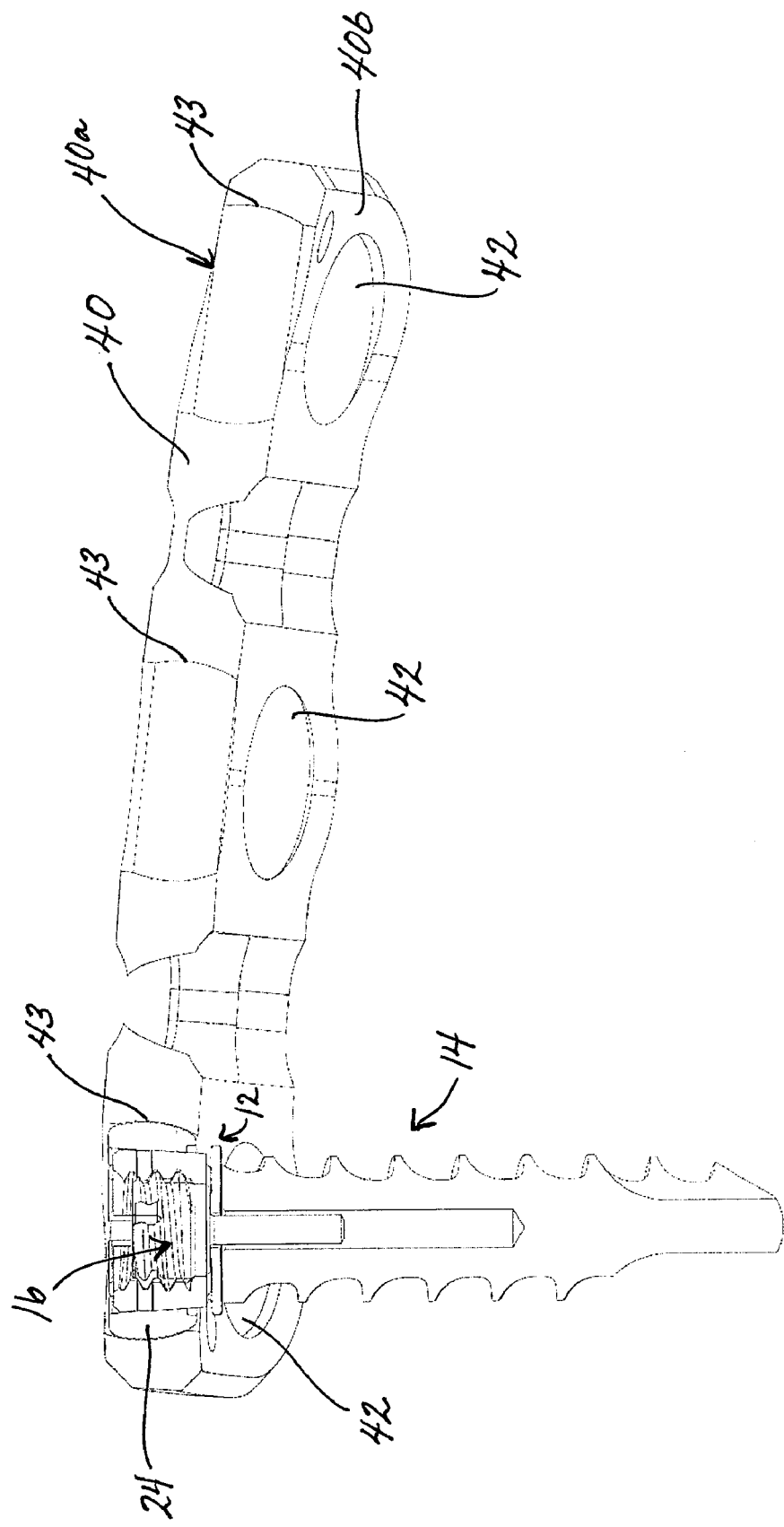
FIG. 4A is a cross-sectional view of one embodiment of a spinal plate having the spinal anchor shown in FIG. 1 disposed therein.
Figure 4B:
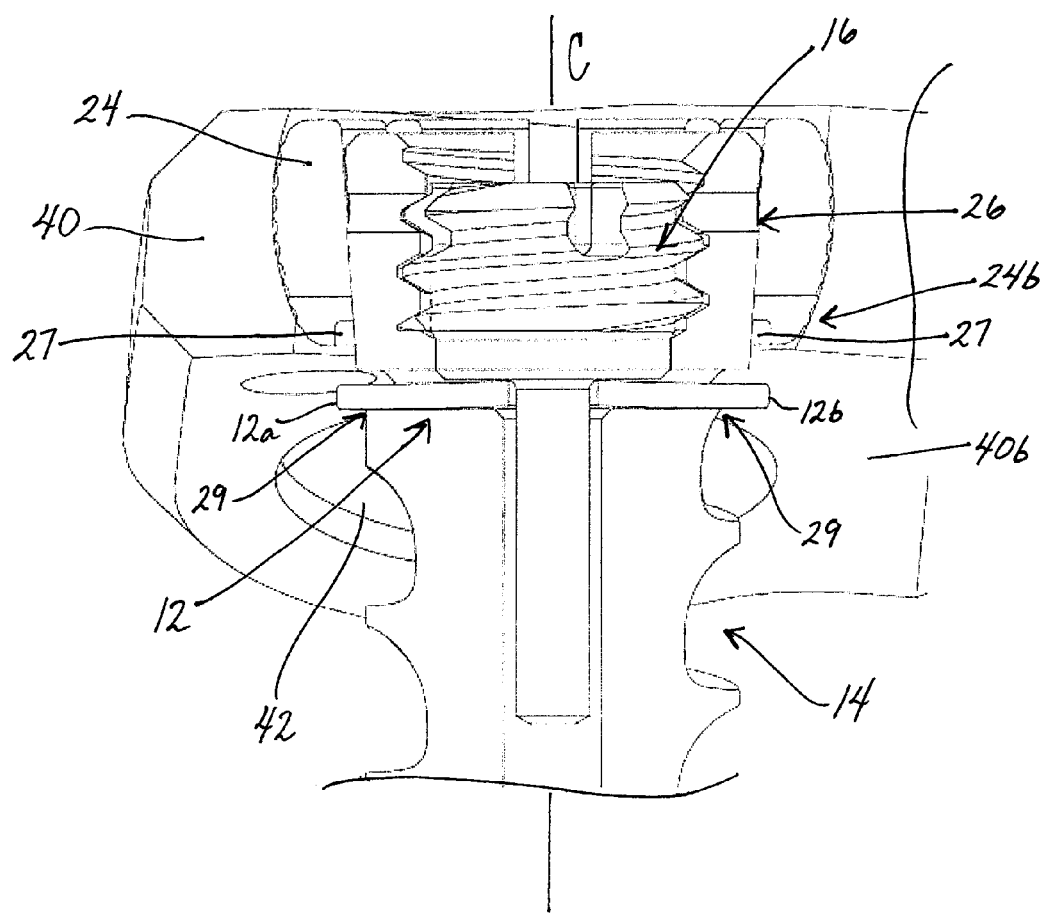
FIG. 4B is a cross-sectional view of a proximal portion of the spinal anchor shown in FIG. 4A as it is received by a thru-bore of the spinal plate shown in FIG. 4A showing the anti-backout mechanism in a deployed position.

The bone engaging fastener 14 can have a variety of configurations, and various bone engaging fasteners; such as hooks, bolts, etc., can be used. In the illustrated embodiment, the bone engaging fastener 14 includes a shank 18 with a head 20 formed thereon. The shank 18 extends distally from the head 20 and includes threads 19 formed thereon and extending between proximal and distal ends 18a, 18b of the shank 18. The head 20 can be sized to be at least partially received within a thru-bore 42 in a spinal plate 40 (FIGS. 4A and 4B).

As further shown in FIG. 1, the head 20 of the bone engaging fastener 14 can include a longitudinally extending bore 22 formed therein for receiving a locking mechanism 16. The bore 22 can be generally sized and shaped to receive the locking mechanism 16 therein. FIG. 1 illustrates one exemplary embodiment of a bore 22 having a stepped diameter. In particular, a proximal portion 22a of the bore 22 is formed in the head 20 of the fastener 14 and has a diameter that is greater than a diameter of a distal portion 22b of the bore 22 which is formed in the shank 18 of the fastener 14. Such a configuration can allow a proximal portion of the locking mechanism 16 to mate within the proximal portion 22a of the bore 22 and to allow a distal portion 38 of the locking mechanism 16 to extend into the distal portion 22b of the bore 22 so as to initially align of the locking mechanism 16 with the bore 22. The proximal portion 22a of the bore 22 can have threads 23 or other mating elements formed therein to facilitate mating to complementary threads or other mating elements formed on the locking mechanism 16.

In one exemplary embodiment, the head 20 of the bone engaging fastener 14 can be configured to expand when the locking mechanism 16 is mated thereto. Expansion of the head 20 of the bone engaging fastener 14 can allow the head 20 to engage a thru-bore in a plate or in a bushing 24 disposed in a thru-bore in a plate. A variety of techniques can be used to allow the head 20 to expand. For example, in one exemplary embodiment one or more cut-outs 35 can be formed in the proximal end 20a of the head 20. The cut-outs 35 can extend longitudinally along at least a portion of the head 20 to allow the head 20 to expand when the locking mechanism 16 is mated thereto. The head 20 can also be tapered to facilitate engagement between the head 20 and a thru-bore in a plate or bushing.

Figure 2B:
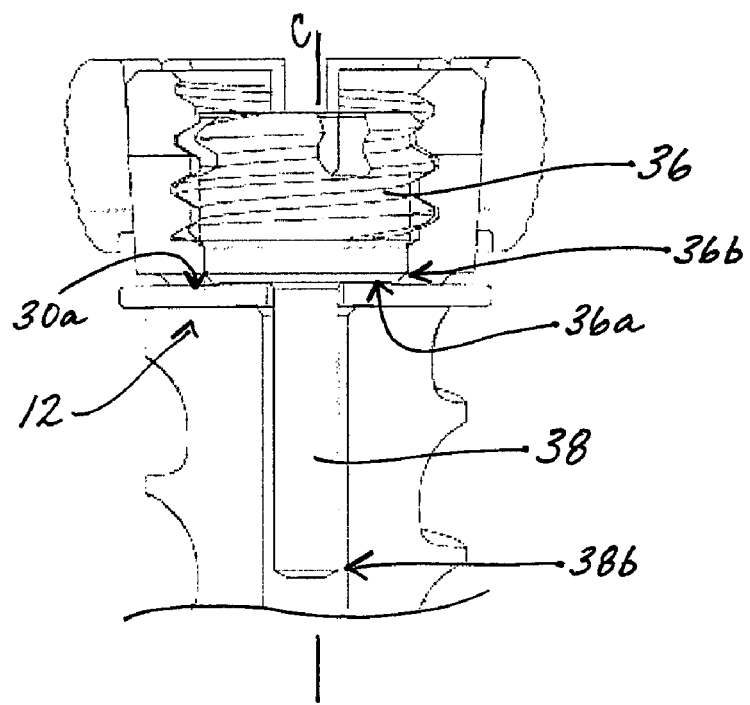
FIG. 2B is a cross-sectional view of a proximal portion of the spinal anchor shown in FIG. 1 showing the anti-backout mechanism extending from the spinal anchor in a deployed position.

The bone engaging fastener 14 can also include a cavity 28 formed therein for seating the anti-backout mechanism 12. The cavity 28 can be formed at various locations in the fastener 14, but in an exemplary embodiment, the cavity 28 is formed in the head 20 or between the head 20 and the shank 18 of the fastener 14. The cavity 28 can have a variety of configurations, and the configuration can vary depending on the anti-backout mechanism 12. As shown in FIGS. 2A and 2B, the cavity 28 is formed at a location just distal to the threads formed in the proximal portion 22a of the bore 22 formed in the head 20. In other words, the cavity 28 can generally be a non-threaded distal portion of the proximal portion 22a of the bore 22. The cavity 28 can also include cut-outs 29 extending therefrom through opposed sidewalls of the fastener. For example, as shown the cut-outs 29 extend substantially perpendicular to the longitudinal axis C of the fastener 14 and they extend radially outward from the bore 22 to form openings in the sidewalls of the fastener 14. The cut-outs 29 can be configured to receive opposed ends 12a, 12b of the anti-backout mechanism 12, and to allow the anti-backout mechanism 12 to extend radially outward from the bone engaging fastener 14 upon deployment. The cut-outs 29 can have a shape and width that generally corresponds with the shape and width of at least the terminal end portions of the anti-backout mechanism 12 disposed therein. As shown in FIGS. 2A and 2B, the cut-outs 29 have a generally rectangular cross-section.

As indicated above, an anti-backout mechanism 12 can be disposed within the cavity 28 of the bone engaging fastener 14. In an exemplary embodiment, the anti-backout mechanism 12 can be biased to a retracted position in which the anti-backout mechanism is retracted or fully contained within the bone engaging fastener 14. As shown in FIGS. 2A and 2B, the anti-backout mechanism 12 is movable between the retracted position (FIG. 2A) and the deployed position (FIG. 2B) in which the anti-backout mechanism protrudes outward from the bone engaging fastener 14. A variety of configurations are available for the anti-backout mechanism 12. For example, in one exemplary embodiment, the anti-backout mechanism 12 can be a flexible member such as a spring. The particular configuration of the spring can vary, but the illustrated spring is a leaf spring 30 that is substantially rectangular and planar except for a bend or pinch 32 formed at a substantial midpoint thereof. The spring 30 can be in a natural state in the bent, retracted position. This can be achieved using, for example, nitinol. Thus, as shown in FIGS. 1 and 2A, the bend in the spring 30 allows the spring 30 to be fully contained within the cavity 28 of the bone engaging fastener 14. In this position, the opposed ends 12a, 12b of the spring 30 do not protrude from the cut-outs 29, but rather are contained within the cut-outs 29. This allows the fastener 14 to be inserted into a thru-bore in a plate or bushing without interference from the spring 30. In the retracted position, the bend 32 can also extend upward into the threaded proximal portion 22a of the bore 22. This will allow the locking mechanism 16 to contact the bent portion when it is applied to the head 20, as will be discussed below. FIG. 2B illustrates the spring 30 in the deployed position. As shown, the spring 30 is compressed such that it is substantially planar and is no longer in a natural state. In the deployed position, the spring 30 can extend substantially perpendicular to the central axis C of the bone engaging fastener and the opposed ends of the spring 30 can extend radially outward from the cut-outs 29 formed in the opposed sidewalls of the bone engaging fastener 14. The spring 30 can also include a bore 34 formed therethrough for receiving a portion of the locking mechanism 16, as discussed below.

As indicated above, the locking mechanism 16 can be mated to the bone engaging fastener 14 to move the anti-backout mechanism 12 from the retracted position to the deployed position. Several configurations are available for the locking mechanism 16. FIGS. 1-3A illustrate one exemplary embodiment of a locking mechanism 16 that generally includes a set screw 36 having an alignment mechanism in the form of an elongate member 38 extending distally therefrom. As shown in FIG. 1, the elongate member 38 is received by the distal portion 22b of the bore 22 formed in the bone engaging fastener 14, and the set screw 36 is threadably mated to the threads in the proximal portion 22a of the bore 22. As indicated above, the anti-backout mechanism 12 can include a bore 34 formed therethrough for allowing the elongate member 38 to extend into the distal portion 22b of the bore 22 in the fastener 14. This will also allow a distal facing surface 36a of the set screw 36 to abut a proximal facing surface 30a of the anti-backout mechanism 12. The locking mechanism 16 can be configured to apply a distally directed force to the anti-backout mechanism 12, and in particular to the bent portion of the anti-backout mechanism 12 that extends into the proximal portion 22a of the bore 22, when the locking mechanism 16 is disposed within the bore 22 of the bone engaging fastener 14 to move the anti-backout mechanism 12 to the deployed position. In particular, as the locking mechanism 16 is threadably mated to the bone engaging fastener 14 the distal facing surface 36a of the set screw 36 can apply a distally directed force to the proximal facing surface 30a of the anti-backout mechanism 12 to compress the bent portion of the anti-backout mechanism 12 such that it deforms to a substantially planar configuration, causing the opposed ends 12a, 12b to extend from the bone engaging fastener 14. A person skilled in the art will appreciate that the locking mechanism need not include an alignment mechanism, and that other locking mechanism can be used in a similar manner to deploy the anti-backout mechanism.

Figure 3A:
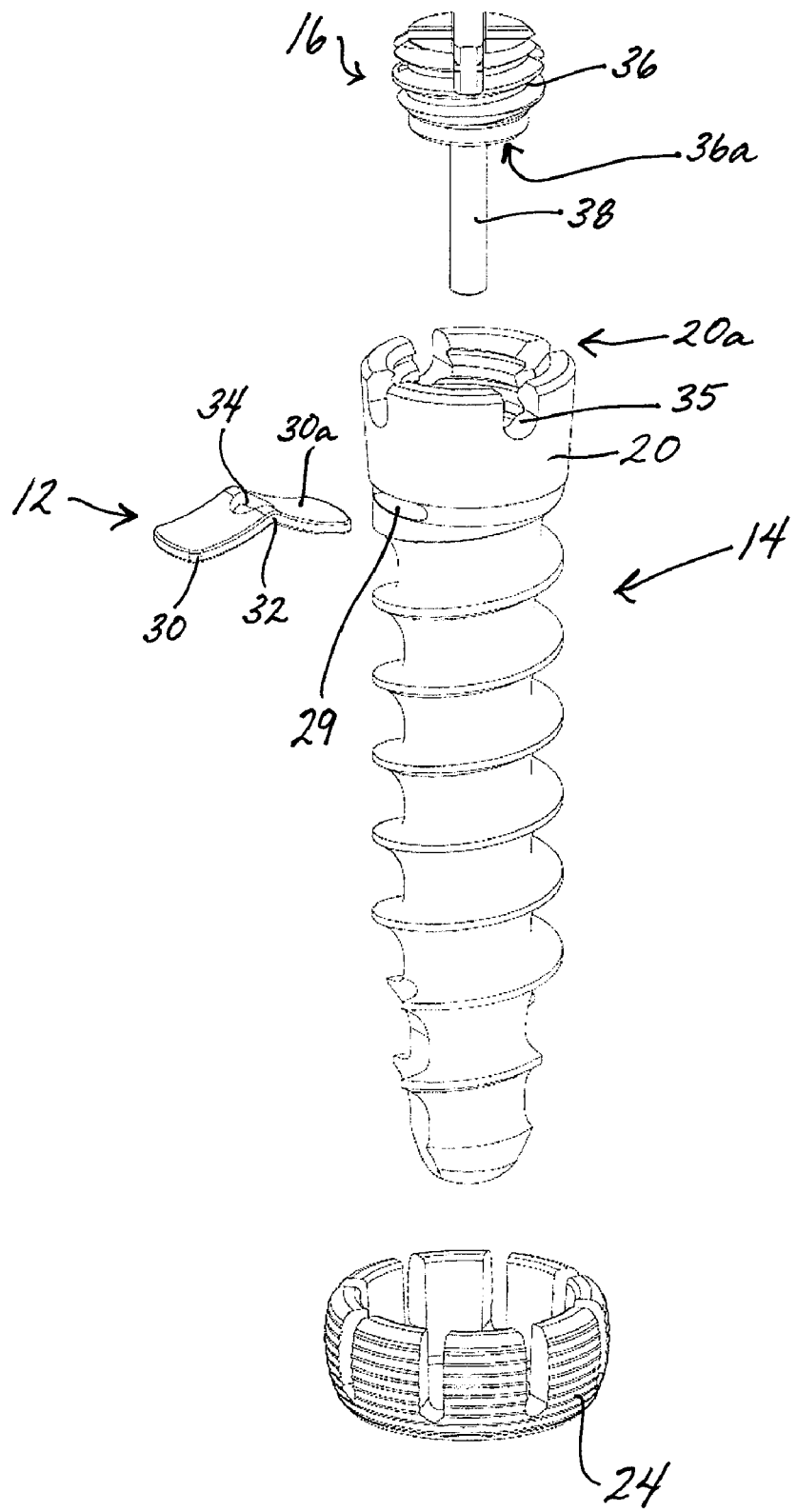
FIG. 3A is an exploded perspective view of the spinal anchor of FIG. 1.
Figure 3B:
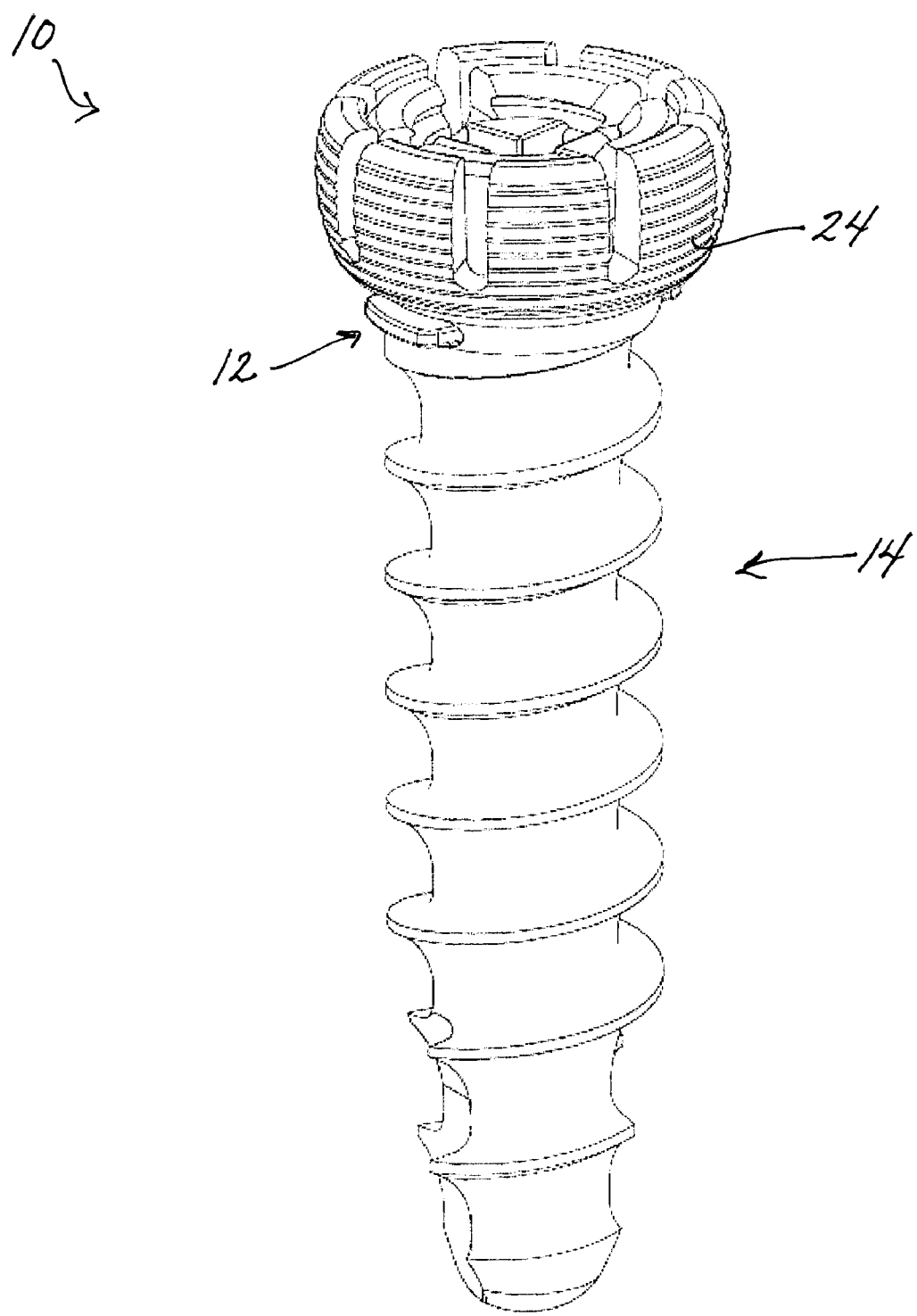
FIG. 3B is an assembled perspective view of the spinal anchor shown in FIG. 3A.

In use, the anti-backout mechanism 12 can prevent the bone engaging fastener 14 from backing out of a thru-bore in a spinal plate 40 such that the bone engaging fastener 14 is locked within the thru-bore 42 in the spinal plate 40. In particular, the bone engaging fastener 14 can be inserted through a thru-bore 42 in a spinal plate 40, which may or may not contain a bushing. A variety of bushings can be disposed within the thru-bore 42 in the plate 40 including, but not limited to, ring-shaped bushings or C-shaped bushings having split, slot, and/or cut-out configurations. FIGS. 3A and 3B illustrate one exemplary embodiment of a bushing 24 that can be configured to seat the head 20 of the bone engaging fastener 14. As shown, the bushing 24 has a ring-shaped configuration with multiple cut-outs formed therein to allow radial compression and/or expansion thereof. An outer surface 25 of the bushing 24 can be sized and shaped to match the inner surface 43 of a thru-bore 42 in a spinal plate 40 (FIGS. 4A and 4B). As shown in FIGS. 1-4B, the outer surface 25 of the bushing 24 has a generally convex spherical shape and can be seated within a thru-bore 42 having a generally concave spherical inner surface 43. The outer surface 25 of the bushing 24 can also include surface features formed thereon to facilitate a frictional engagement with the thru-bore 42 in a spinal plate 40. FIGS. 3A and 3B illustrates ridges extending radially around the bushing 24. A variety of other surface features or textures can be used to facilitate engagement between the bushing 24 and a thru-bore 42, or alternatively the bushing 24 can have a smooth outer surface. The inner surface of the bushing 24 can also have a variety of configurations, but in an exemplary embodiment the inner surface has a diameter that decreases from the proximal end 24a to the distal end 24b such that the thru-bore of the bushing 24 is tapered. The distal end 24b of the thru-bore 26 formed in the bushing 24 can include a groove or undercut 27 (FIG. 4B) that is configured to receive and seat the anti-backout mechanism 12 when it is in the deployed position. The undercut 27 can have a depth and width that corresponds to the depth and width of the anti-backout mechanism 12 to enable the anti-backout mechanism 12 to sit therein such that the anti-backout mechanism 12 is flush with the distal surface of the plate, as will be described in detail below.

FIG. 4A illustrates one exemplary embodiment of a spinal plate 40 that can be used with the bone engaging fastener 14. As shown, the spinal plate 40 has a generally planar or slight curved configuration with a first, superior surface 40a and a second, inferior bone contacting surface 40b. The spinal plate 40 can include any number of thru-bores 42 formed therein and extending between the superior and inferior surfaces 40a, 40b. The plate 40 can also include additional features to facilitate use of the spinal anchor 10. The thru-bore(s) 42 can be sized and shaped to seat a bushing 24 therein such that, when a bone engaging fastener 14 is inserted through a thru-bore 42 in the plate 40, an interference fit is created between the head 20 of the bone engaging fastener 14, the bushing 24, and the thru-bore 42 in the plate 40. Alternatively, the thru-bore(s) 42 can be sized and shaped to directly receive the fastener 14 without the use of a bushing 24.

In use, the spinal plate 40 can be positioned against a bone surface, such as against a vertebra in a spinal column (not shown). Once the bone is prepared, e.g., by drilling, tapping, etc., the bone engaging fastener 14 can be inserted or passed through a thru-bore 42 in the spinal plate 40 (with or without a bushing disposed therein) and threaded into bone. FIGS. 4A and 4B illustrate the bone engaging fastener 14 disposed through a bushing 24 which is seated within a thru-bore 42 in the plate 40.

Once the bone engaging fastener 14 is threaded into bone, the locking mechanism 16 can be applied to the fastener 14 to deploy the anti-backout mechanism 12 disposed therein. For example, applying the locking mechanism 16 can include threading the locking mechanism 16 into the bore 22 formed in the head 20 of the bone engaging fastener 14. As the locking mechanism 16 is threaded into the head 20, the elongate member 38 will extend into the distal portion 22b of the bore 22 in the fastener 14 to maintain alignment between the locking mechanism 16 and the bore 22. In one exemplary embodiment, the bone engaging fastener 14 and the locking mechanism 16 can be configured such that the same tool can be used to secure the bone engaging fastener 14 within bone as well as apply the locking mechanism 16 to the bone engaging fastener 14. In another embodiment, the bone engaging fastener 14 and the locking mechanism 16 can be configured such that separate tools can be used to apply the bone engaging fastener 14 and the locking mechanism 16. For example, the head 20 of the fastener 14 and the set screw 36 on the locking mechanism 16 can each include a drive feature, such as one or more slits formed therein, for receiving a driver. The drive features can be the same to allow for use of a single driver, or they can differ such that a first driver can be used to drive the bone engaging fastener 14 into bone, and a separate driver can be used to apply the locking mechanism 16 to the bone engaging fastener 14. Applying the locking mechanism 16 can be effective to cause the anti-backout mechanism 12 to extend outward from the bone engaging fastener 14 to thereby prevent the bone engaging fastener 14 from backing out of the thru-bore 42 such that the bone engaging fastener 14 is locked within the thru-bore 42 in the spinal plate 40. In particular, as the locking mechanism 16 is applied to the bone engaging fastener 14, the locking mechanism 16 can apply a distally directed force to the anti-backout mechanism 12 to cause the anti-backout mechanism 12 to move from the retracted position in which the anti-backout mechanism 12 is fully contained within the bone engaging fastener 14 to the deployed position in which the anti-backout mechanism 12 extends outward from the bone engaging fastener 14. In an exemplary embodiment, the head 20 of the bone engaging fastener 14 can be configured such that application of the locking mechanism 16 is also effective to expand the head 20 of the bone engaging fastener 14 to engage the bushing 24 disposed therearound and seated in the thru-bore 42 in the spinal plate 40.

As shown in FIGS. 4A and 4B, applying the locking mechanism 16 causes the anti-backout mechanism 12 to become substantially planar such that opposed ends 12a, 12b of the anti-backout mechanism 12 extend from the cut-outs 29 formed in opposed sidewalls of the bone engaging fastener 14. In one exemplary embodiment, the deployed anti-backout mechanism 12 can engage a bone contacting surface 40b of the spinal plate to thereby prevent the bone engaging fastener 14 from backing out of the thru-bore 42 in the spinal plate 40. In another embodiment, shown in FIGS. 4A and 4B, the deployed anti-backout mechanism 12 can be configured to engage a bone contacting surface of the bushing 24, and/or to be received by a groove or undercut 27 formed in the distal end 24b of the thru-bore 26 formed in the bushing 24, as indicated above. Since the bushing 24 is locked within the thru-bore 42 by the expanded head of the fastener 14, the anti-backout mechanism 12 will engage the bushing 24 to prevent the bone engaging fastener 14 from backing out of the thru-bore 26 in the bushing 24 thereby preventing the fastener 14 from backing out of the thru-bore 42 in the spinal plate 40. Such a configuration can lock the fastener 14 within the thru-bore 42 in the spinal plate 40. The undercut 27 can also allow the anti-backout mechanism 12 to sit flush with the bone-contacting surface of the spinal plate 40. A person skilled in the art will appreciate that, while the plate and bushing are described as having bone-contacting surfaces, the surfaces can merely face the bone and do not necessarily need to come into direct contact with the bone.

In order to remove the bone engaging fastener 14 from the spinal plate 40, the locking mechanism 16 can be simply unthreaded. Unthreading the locking mechanism 16 can be effective to remove the distally directed force applied to the anti-backout mechanism 12 thereby allowing the anti-backout 12 to return to its natural state in which it is retracted within the cavity 28 of the bone engaging fastener 14. Thus, the anti-backout mechanism 12 disclosed herein provides a reversible means for locking a bone engaging fastener 14 within a thru-bore 42 in a spinal plate 40.

A person skilled in the art will appreciate that the various methods and devices disclosed herein can be formed from a variety of materials. Moreover, particular components can be implantable and in such embodiments the components can be formed from various biocompatible materials known in the art. Exemplary biocompatible materials include, by way of non-limiting example, composite plastic materials, biocompatible metals and alloys such as stainless steel, titanium, titanium alloys and cobalt-chromium alloys, and any other material that is biologically compatible and non-toxic to the human body.

One skilled in the art will appreciate further features and advantages based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A spinal anchor, comprising:
   a bone engaging fastener having a threaded shank with a head formed thereon and configured to sit in a thru-bore in a spinal plate;
   an anti-backout mechanism disposed within the head of the bone engaging fastener and movable between a retracted position in which the anti-backout mechanism is retracted into the bone engaging fastener, and a deployed position in which the anti-backout mechanism extends from the bone engaging fastener, the anti-backout mechanism being biased to the retracted position; and
   a locking mechanism matable to the bone engaging fastener and configured to move the anti-backout mechanism from the retracted position to the deployed position;

wherein the locking mechanism includes an elongate member extending distally therefrom such that the elongate member extends through the anti-backout mechanism to maintain alignment between the locking mechanism and the bone engaging fastener; and wherein the anti-backout mechanism comprises a leaf spring.

2. The spinal anchor of claim 1, wherein the locking mechanism is configured to apply a distally directed force to the anti-backout mechanism when the locking mechanism is mated to the bone engaging fastener to move the anti-backout mechanism to the deployed configuration.

3. The spinal anchor of claim 1, wherein the leaf spring is in a natural state in the retracted position.

4. The spinal anchor of claim 1, wherein the anti-backout mechanism is substantially planar in the deployed configuration.

5. The spinal anchor of claim 1, wherein the locking mechanism comprises a set screw and the head includes a bore formed therein for receiving the locking mechanism.

6. The spinal anchor of claim 1, wherein the bone engaging fastener includes cut-outs extending through opposed sidewalls thereof for allowing opposed ends of the anti-backout mechanism to extend from the bone engaging fastener when the anti-backout mechanism is in the deployed position.

7. The spinal anchor of claim 1, wherein the anti-backout mechanism extends substantially perpendicular to a central axis of the bone engaging fastener.

8. The spinal anchor of claim 1, further comprising a bushing disposed around the head of the bone engaging fastener.

9. The spinal anchor of claim 8, wherein the head is configured to expand and engage the bushing when the locking mechanism is mated to the bone engaging fastener.

10. A spinal fixation kit, comprising:
    a spinal plate having at least one thru-bore formed therein;
    a bone engaging fastener having a head disposable within the at least one thru-bore in the spinal plate and having an anti-backout mechanism disposed therein; and
    a locking mechanism matable to the bone engaging fastener and configured to cause the anti-backout mechanism to extend from the bone engaging fastener to engage at least one of the spinal plate and a bushing disposed within the spinal plate when the head is seated therein to prevent the bone engaging fastener from backing out of the thru-bore in the spinal plate;
    wherein a distal portion of the locking mechanism is configured to extend through a bore formed in the anti backout mechanism to maintain alignment between the locking mechanism and the bone engaging fastener; and
    wherein the anti-backout mechanism comprises a leaf spring.

11. The spinal fixation kit of claim 10, wherein the anti-backout mechanism is biased to a retracted position in which the anti-backout mechanism is fully contained within the bone engaging fastener.

12. The spinal fixation kit of claim 10, wherein the anti-backout mechanism is substantially planar when the anti-backout mechanism extends from the bone engaging fastener.

13. The spinal fixation kit of claim 10, wherein the bone engaging fastener includes cut-outs extending through opposed sidewalls thereof for allowing opposed ends of the anti-backout mechanism to extend from the bone engaging fastener.

14. The spinal fixation kit of claim 10, wherein the anti-backout mechanism extends substantially perpendicular to an axis of the bone engaging fastener.

15. The spinal fixation kit of claim 10, further comprising a bushing disposed within the at least one thru-bore in the plate and configured to seat a portion of the bone engaging fastener.

16. The spinal fixation kit of claim 10, wherein the locking mechanism is configured to apply a distally directed force to the anti-backout mechanism when the locking mechanism is mated to the bone engaging fastener to cause the anti-backout mechanism to extend from the bone engaging fastener.

17. A spinal anchor, comprising:
    a bone engaging fastener having a shank with a head formed thereon and configured to sit in a thru-bore in a spinal plate;
    an anti-backout mechanism disposed within the bone engaging fastener and movable between a retracted position in which the anti-backout mechanism is retracted into the bone engaging fastener, and a deployed position in which the anti-backout mechanism extends from the bone engaging fastener, the anti-backout mechanism being biased to the retracted position; and
    a set screw having an elongate member extending distally therefrom, the set screw being matable to the bone engaging fastener such that distal advancement of the set screw within the bone engaging fastener causes the anti-backout mechanism to move from the retracted position to the deployed position;
    wherein the elongate member extends through the anti-backout mechanism to maintain alignment between the set screw and the bone engaging fastener; and
    wherein the anti-backout mechanism comprises a leaf spring.

18. The spinal anchor of claim 1, wherein the elongate member is configured to extend through a bore formed in the anti-backout mechanism and into a longitudinally extending bore formed in the shank of the fastener.

19. The spinal fixation kit of claim 10, wherein the distal portion of the locking mechanism is configured to extend through the bore formed in the anti-backout mechanism and into a longitudinally extending bore formed in the fastener.

20. The spinal anchor of claim 17, wherein the elongate member is configured to extend through a bore formed in the anti-backout mechanism and into a longitudinally extending bore formed in the shank of the fastener.

* * * * *